United States Patent
Hoekstra et al.

(10) Patent No.: US 10,046,069 B2
(45) Date of Patent: Aug. 14, 2018

(54) AMORPHOUS CARBON SUPPORTED NANOPARTICLES COMPRISING OXIDES OF LANTHANIDES AND METHOD FOR PREPARING THEM

(71) Applicant: BASF Corporation, Florham Park, NJ (US)

(72) Inventors: Jacobus Hoekstra, De Meern (NL); Eefjan Breukink, De Meern (NL); Leonardus Wijnand Jenneskens, De Meern (NL); John Wilhelm Geus, De Meern (NL)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 15/665,844

(22) Filed: Aug. 1, 2017

(65) Prior Publication Data
US 2017/0354749 A1    Dec. 14, 2017

Related U.S. Application Data

(62) Division of application No. 14/387,893, filed as application No. PCT/IB2013/052457 on Mar. 27, 2013, now Pat. No. 9,750,828.

(30) Foreign Application Priority Data

Mar. 29, 2012   (EP) ..................... 12162272

(51) Int. Cl.
*A61K 51/00*   (2006.01)
*A61K 51/12*   (2006.01)

(52) U.S. Cl.
CPC ...... *A61K 51/1251* (2013.01); *A61K 51/1244* (2013.01)

(58) Field of Classification Search
CPC .................. A61K 51/1244; A61K 51/1251
See application file for complete search history.

(56) References Cited

U.S. PATENT DOCUMENTS

| 5,261,956 A | 11/1993 | Dunaway et al. |
| 2008/0292530 A1 | 11/2008 | Keller et al. |
| 2009/0258076 A1 | 10/2009 | Cheon et al. |

FOREIGN PATENT DOCUMENTS

| CN | 1259488 | 7/2000 |
| EP | 2383374 | 11/2011 |

OTHER PUBLICATIONS

Research Papers Center, http://big.hi138.com/gongxue/cailiaogongcheng/200906/61319.asp, 6 pages.
(Continued)

*Primary Examiner* — Ernst V Arnold
(74) *Attorney, Agent, or Firm* — Lowenstein Sandler LLP

(57) ABSTRACT

The invention is directed to bodies comprising an amorphous carbon particle on which are supported nanoparticles of an oxide of lanthanide. These bodies find use as a pharmaceutical for use in a surgery or therapy and diagnostic methods. The bodies can be made by a process comprising impregnating a carbon source material by contacting it with a solution of a salt of the lanthanide; drying the impregnated carbon source material; and subjecting the dried impregnated material to pyrolysis under inert conditions.

16 Claims, 3 Drawing Sheets

(56) References Cited

OTHER PUBLICATIONS

Zhang et al: "Preparation and 1,2,4 characterization of La2O3 doped diamond-like carbon nanofilms (I) Structure analysis", Diamond and Related Materials, Elsevier Science Publishers, Amsterdam, NL vol. 16, No. 11, Oct. 18, 2007 (Oct. 18, 2007) pp. 1905-1911, XP022303882, ISSN: 0925-9635 abstract.

Miyawaki J et al: "Synthesis of Ultrafine Gd2O3 Nanoparticles Inside Single-Wall Carbon Nanohorns", Journal of Physical Chemistry. B (Online), American Chemical Society, Columbus, OH, US. Jan. 1, 2006 (Jan. 1, 2006), pp. 5179-5181, XP003007791, ISSN: 1520-5207, DOI: 10.1021/JP0607622 abstract p. 5180, col. 2, paragraph 3.

Jacco Hoekstra et al: "A new procedure to produce carbon-supported metal catalysts" In: "Scientific Bases for the Preparation of Heterogeneous Catalysts—Proceedings of the 10th International Symposium, Louvain-la-Neuve, Belgium, Jul. 11-15, 2010". Jan. 1, 2010 (Jan. 1, 2010), Elsevier, XP055033886, ISSN: 0167-2991 ISBN: 978-0-44-453601-3 vol. 175, pp. 93-100, DOI: 10.1016/S0167-2991(10)75012-6, abstract p. 94, paragraph 4-paragraph 7.

Vente M A D et al: "Holmium-166 poly(L-lactic acid) microsphere radioembolisation of the liver: technical aspects studied in a large animal model", European Radiology, Springer, Berlin, DE, vol. 20, No. 4, Sep. 30, 2009 (Sep. 30, 2009), pp. 862-869, XP019801274, ISSN: 1432-1084 abstract p. 865, col. 2, paragraph 4—p. 868, col. 2, paragraph 2.

International Search Report—PCT/IB2013/052457 dated Aug. 21, 2013, 4 pages.

Feng et al. (Journal of the Chinese Ceramic Society, Mar. 2011, 39(3):397-402.

Zhang et al. "Carbon Nanotube Assisted Synthesis of CeO2 Nanotubes" (Journal of Solid State Chemistry 2007;180:654-660).

Written Opinion of the International Searching Authority (PCT Rule 43bis.1) for PCT/IB2013/052457, 5 pages.

Sun et al. "Coating Carbon Nanotubes with Metal Oxides in a Supercritical Carbon Dioxide-Ethanol Solution" (Carbon 2007;45:2589-2596).

Yermakov et al. React Kinet Catal Lett 1987;33(2):435-440).

Carbon black [online] retrieved on Jun. 1, 2016 from http://thefreedictionary.com/carbon+black; 2pages.

Ryndin et al. (React Kinet Catal Lett 1991;44(2):303-308).

English translation of WO 2007131795 2007; 5 pages.

Ryndin, et al, "Supported Metallic Catalysts Obtained by Anchoring Metal Complexes on Carbon Supports", Journal of Molecular Catalysis, 1989, p. 109-125, vol. 55, 18 pages.

Saucerman (Carbon 2004; The Rosen Publishing Group p. 21; 1 page).

Zerda (Structure of Carbon Black Particles in High Pressure Molecular Science 2012 Springer Science & Business Media pp. 225-226; 2 pages).

Carbon black [online] retrieved on Jun. 1, 2016 from: http://www.britannica.com/science/carbon-black; 2 pages.

Salzmann et al. "The Role of Carboxylated Carbonaceous Fragments in the Functionalization and Spectroscopy of a Single-Walled Carbon-Nanotube Material" (Advanced Materials 2007;19:883-887).

Carbon Materials for Catalysis, eds. Serp, Figueiredo, p. 435, section 12.2.3 "Carbons of the Sibunit family", Wiley, 2009, ISBN 978-470-17855-0.

Rhim et al. "Changes in Electrical and Microstructural Properties of Microcrystalline Cellulose as Function of Carbonization Temperature" (Carbon 2010(48):1012-1024) 13 pages.

International Search Report and Written Opinion—PCT/IB2013/052457, dated Oct. 1, 2014, 6 pages.

AMORPHOUS CARBON SUPPORTED NANOPARTICLES COMPRISING OXIDES OF LANTHANIDES AND METHOD FOR PREPARING THEM

The invention is directed to bodies comprising small particles (nanoparticles) of oxides of lanthanides, in particular holmium oxide ($Ho_2O_3$), which are supported on amorphous carbon particles. The invention is further directed to processes for producing these bodies of carbon supported nanoparticles, as well as to the use of these bodies of carbon supported nanoparticles in therapeutic applications.

Lanthanides, particularly holmium, can be used in radio-embolization therapy of liver metastases. Upon neutron irradiation $^{165}$Ho is converted to $^{166}$Ho which is a beta-radiation emitter. The radio-active holmium has shown promising results in the radio-ablation treatment of tumors. Intratumoral injections of $^{166}$Ho(NO$_3$)$_3$ in a rat model of malignant melanoma has shown promising results (see Lee, J. D. et al., Eur. J. Nucl. Med. 29 (2002) 221-230).

Holmium is attractive since it is both a beta- and gamma-emitter when irradiated to Holmium-166 ($^{166}$Ho). Therefore it can be used both in nuclear imaging and radio ablation. Moreover, holmium can be visualized by computed tomography and MRI due to its high attenuation coefficient and paramagnetic properties, as described for instance by Bult, W. et al., Pharmaceut. Res. 26(2009) 1371. Poly(L-lactic acid) (PLLA) microspheres are known in the art, which are loaded with holmium acetylacetonate (HoACAC) (Nijsen, J. F. W. et al., Eur. J. Nucl. Med. 26 (1999) 699-704). The PLLA coating was used to make the HoACAC biocompatible. By administration of these radioactive microspheres into the hepatic artery, they become trapped in the liver, particularly in and around tumors.

A drawback in the use of the PLLA coating is the sensitivity to neutron radiation, which can result in damage of the coating, see Nijsen, J. F. W. et al., Biomaterials 23 (2002) 1831-1839.

Also known in the art is the synthesis of ultrafine $Gd_2O_3$ nanoparticles inside single-walled carbon nanohorns, as described by Miyawaki, J. et al., Journal of Physical Chemistry B 110 (2006) 5179-5181. The disadvantage of carbon nanohorns is that the methods for producing such materials are difficult to scale up. As a consequence, the cost of using such materials on an industrial level is prohibitively high. Further, Huey-Ing, C. et al., Colloids and Surfaces A: Physiochemical and Engineering Aspects 242 (2004) 61-69) describes a method for preparing cerium dioxide nanoparticles. However, neither document describes that the lanthanide oxide nanoparticles prepared may be supported on amorphous carbon and used in radiotherapy.

An object of the present invention is to provide bodies comprising nanoparticles of one or more oxides of lanthanides, in particular holmium, which are supported by amorphous carbon. A further object is to provide these bodies of carbon particles having nanoparticles of oxides of lanthanides thereon and/or therein, in particular holmium, that may be used in radiotherapy.

It was found that very small particles comprising oxides of lanthanides can be made by allowing said oxides to form in combination with carbon.

Thus in a first aspect, the present invention is directed to a body comprising an amorphous carbon particle having provided thereon nanoparticles of an oxide of lanthanide. Typically nanoparticles have a diameter of 10 nm or less.

The nanoparticles are present on the surface of the porous amorphous carbon particle, which surface includes the (inner) pore area.

An amorphous carbon particle, as defined herein, is a carbon material without long-range crystalline order. Short-range order exists, but with deviations of the interatomic distances and/or interbonding angles with respect to the graphite lattice as well as the diamond lattice, described by E. Fitzer et al., (IUPAC recommendations 1995) Pure & Applied Chemistry, 67 (1995) 473-506.

The nanoparticles can be administered when still supported on and/or present within the amorphous carbon particles. The bodies of amorphous carbon particles comprising the supported nanoparticles can be tailored to any desired size ranging from several tens of nanometers up to one millimeter or more. Typically their size ranges from 10 μm to 1000 μm, preferably from 15-500 μm, more preferably 20-400, and even more preferably 25-250 μm. The size of the bodies may be determined by the size of the starting material. After loading the carbon particles with the nanoparticles in accordance with the present invention, they may be crushed or milled, optionally followed by size separation (such as by sieving and/or separation based on density differences, e.g. in a fluidized bed or so called wind sieving) to obtain bodies of the desired size.

The nanoparticles in the body of the present invention preferably have a diameter of 10 nm or less, more preferably the diameter is 5 nm or less.

The bodies of the present invention may be used as a pharmaceutical. In particular they may be used for treatment of the human or animal body by surgery or therapy and diagnostic methods. Such therapy may for instance comprise radiotherapy, in particular radio-embolization. They can be used for instance in the treatment of liver disorders or kidney disorders, in particular tumors, more in particular metastases.

The bodies of the invention may be functionalized by attaching one or more active groups to the surface of the particles. Because the surface comprises amorphous carbon, it was found that it is relatively easy to attach chemical groups to the surface. Such active groups may be selected from nucleic acids, lipids, fatty acids, carbohydrates, polypeptides, amino acids, proteins, plasma, antibodies, antigens, liposomes, hormones, markers and combinations thereof.

Another advantage of the bodies of the present invention is that since carbon functions as a neutron moderator, the carbon carrier is relatively stable against neutron irradiation.

The lanthanides series comprises the fifteen metallic chemical elements with atomic numbers 57 through 71, i.e. the group consisting of La (atomic number 57), Ce (58), Pr (59), Nd (60), Pm (61), Sm (62), Eu (63), Gd (64), Tb (65), Dy (66), Ho (67), Er (68), Tm (69), Yb (70), and Lu (71) (lanthanum, cerium, praseodymium, neodymium, promethium, samarium, europium, gadolinium, terbium, dysprosium, holmium, erbium, thulium, ytterbium, and lutetium). Preferably $Ho_2O_3$ is used as the oxide of lanthanide.

The bodies are in the form of an amorphous carbon particle, which has pores throughout its volume. On the surface of these pores the nanoparticles are dispersed. One of the advantages of the present invention is that the dispersion of the nanoparticles is very homogeneous.

The diameter of the bodies of the present invention refers to a spherical particle. In case the shape of the bodies deviates from spherical, the diameter refers to the largest dimension of the particle. Preferably the bodies of the present invention are spherical or essentially spherical, in particular having a sphericity of close to 1, for instance more than 0.75, preferably more than 0.85. The sphericity of a certain particle is the ratio of the surface area of a sphere having the same volume as said particle to the surface area of said particle.

Also the nanoparticles of crystalline oxide of lanthanide are typically essentially spherical, viz. having a sphericity of more than 0.85, preferably about 1.

Although the lanthanide oxide particles in the bodies of the present invention are very small, the crystal structure is the same as the normally occurring crystal structure of the bulk oxide material, which is cubic for all oxides of lanthanides.

A homogeneous distribution of the lanthanide oxide precursor is important to produce small metal oxide particles homogeneously distributed throughout the obtained bodies. For this reason the carbon precursor material is contacted, in particular impregnated, with a solution of a salt of the corresponding lanthanide. Aqueous solutions are preferred. Preferably the corresponding lanthanide nitrate is used, because these generally have a good solubility in water. The corresponding $Cl^-$, $Br^-$ and $I^-$ salts could also be used but these are less preferred, since they may give rise to the formation of the corresponding halogen compounds, which is undesired.

The bodies of the present invention may be produced by a process comprising the steps of:
  impregnating a carbon source material by contacting it with a aqueous solution of a salt of said lanthanide;
  drying said impregnated carbon source material; and
  subjecting said dried impregnated material to pyrolysis under inert conditions.

The size of the nanoparticles comprising the crystalline lanthanide oxide on the bodies of the present invention can be controlled by choosing the concentration of lanthanide salt in the aqueous solution. A higher concentration leads to nanoparticles having a larger diameter and a lower concentration to smaller nanoparticles. Typical concentrations are in the range of 0.01-1.5 g/ml, preferably 0.1-1 g/ml, depending on the solubility of the salt.

The carbon source material is a material that contains sufficient carbon atoms to produce essentially carbon containing particles upon pyrolysis. Suitable materials are for instance cellulose, preferably microcrystalline cellulose (MCC, which is for instance described in WO-A-2007/131795, incorporated herein), but also other materials, such as cotton may be used; carbohydrates, such as sugar or chitosan; and active carbon. Very suitable MCC particles are obtainable under the trade name Cellets™, which are available in a broad range of diameters, for instance from 100-200 μm to 1000-1400 μm and which have a sphericity of 0.9 to 0.95.

Typically the drying step is carried out until the dried product reaches constant weight. Preferably the drying is carried out at room temperature (about 25° C.).

The pyrolysis step is carried out by heating the dried impregnated material to a temperature that is sufficient to convert most or all non-carbon material into volatile compounds. This step is carried out under inert conditions, viz. under conditions that avoid reaction of carbon with the surroundings. Preferably these conditions comprise exclusion of oxygen from air. This may preferably be obtained by carrying out the pyrolysis under a typical "inert" gas, such as nitrogen or a noble gas, such as argon or helium, which is used to dissipate the oxygen containing air.

Typically the carbon particles shrink upon pyrolysis, resulting in the bodies of the present invention, for instance by 10-30%, relative to their original diameter.

The process of the present invention may also include a following step wherein the amorphous carbon particle is removed, thereby obtaining nanoparticles in a pure form. Typically the amorphous carbon particle may be removed by oxidation to carbon dioxide. Oxidation with gaseous oxygen can be done by thermal treatment in an oxygen-containing gas flow at a temperature below about 500° C.

The invention will now be illustrated by the following non-limiting example.

EXAMPLE 2 grams of hydrophilic MCC spheres (Cellets™ 100 obtained from Synthapharm, particle size distribution of 100-200 μm) were loaded via wet impregnation. To this end the spheres were immersed in an aqueous solution of holmium nitrate pentahydrate (2 g $Ho(NO_3)_3.5H_2O$, Sigma-Aldrich, 99.9% purity, in 20 ml $H_2O$). The spheres were left for 24 h within the solution with occasional stirring. Next, the impregnated spheres were filtered using a Buchner funnel with glass filter, after which the isolated spheres were dried at 80° C. to constant weight at room temperature. Subsequently pyrolysis was performed at 800° C. under a stagnant nitrogen atmosphere for 3 h. Scanning- and transmission electron microscopy were employed to image the resulting holmium particles and the carbonaceous support. Conventional TEM, as well as electron diffraction patterns were recorded.

Figure 1:
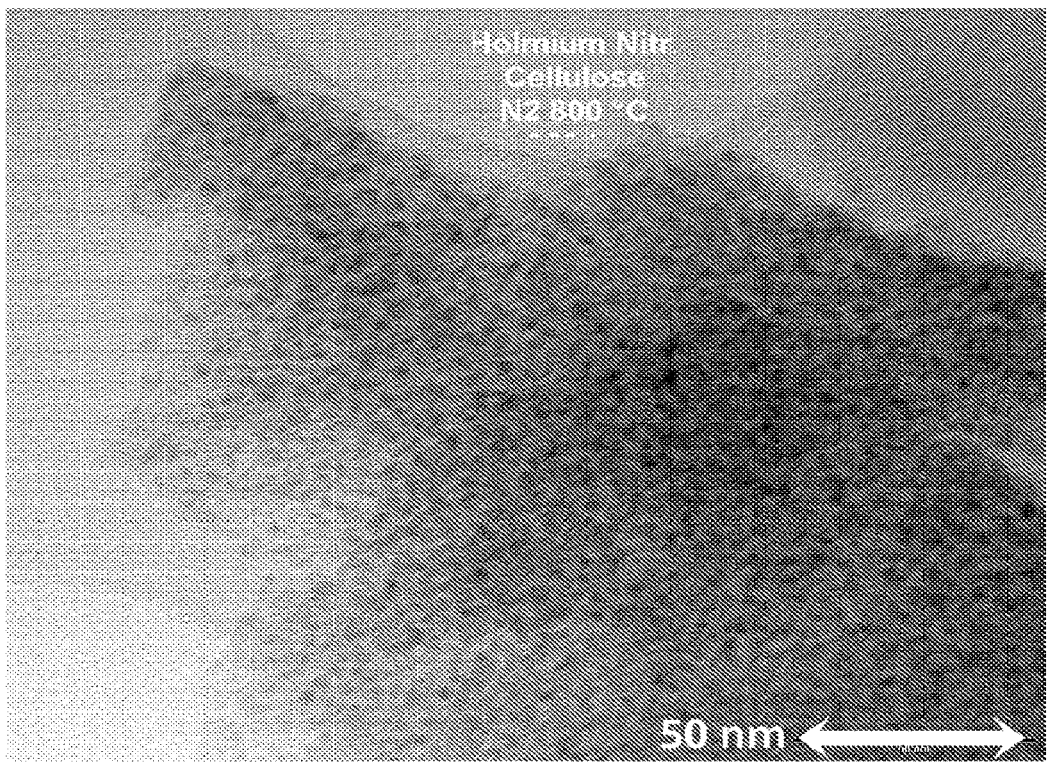
FIG. 1 shows a Transmission Electron Micrograph (TEM) image of a crushed body in accordance with the present invention comprising amorphous carbon particles on which the nanoparticles are supported.
Figure 2:
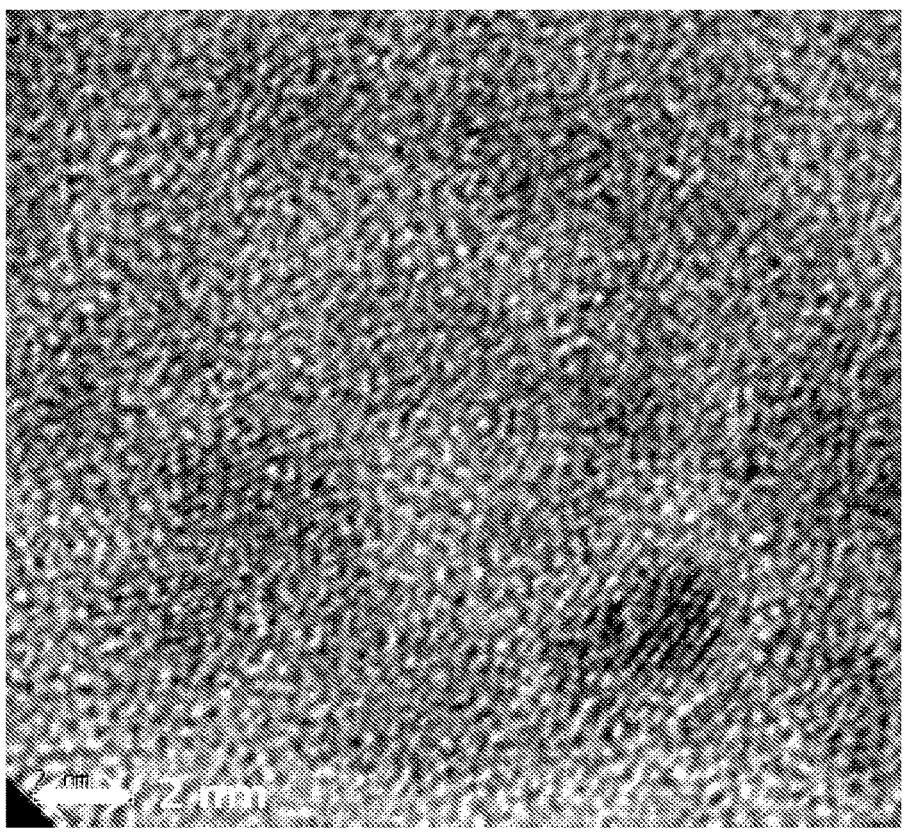
FIG. 2 shows a high resolution TEM (HR-TEM) image of carbon supported holmium oxide particles of the present invention. Lattice fringes are exhibited. The dashed circle in this figure shows a nanoparticle having a diameter of approximately 5 nm.
Figure 3:
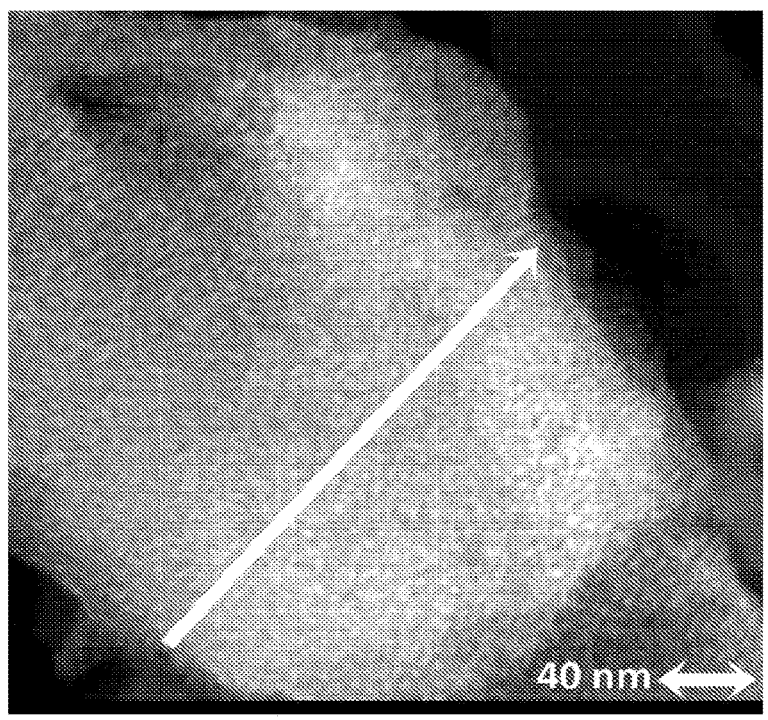
FIG. 3 shows a TEM-image (high angle annular dark field, HAADF) of carbon supported holmium oxide particles of the present invention.
Figure 4:
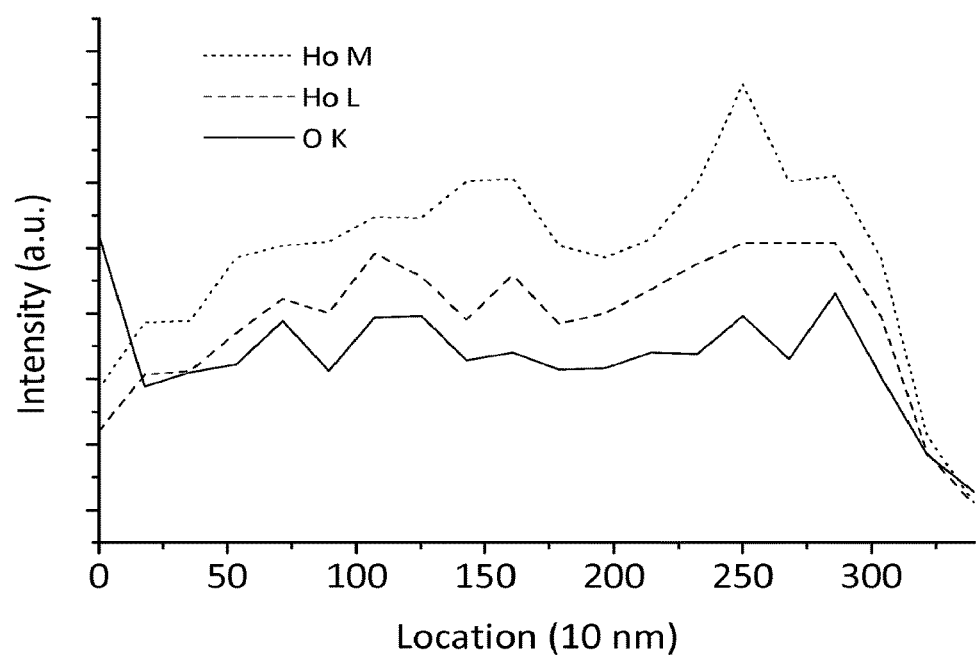
FIG. 4 shows an elemental analysis along the arrow indicated in FIG. 3. The oxygen signal points to holmium oxide nanoparticles.
Figure 5:
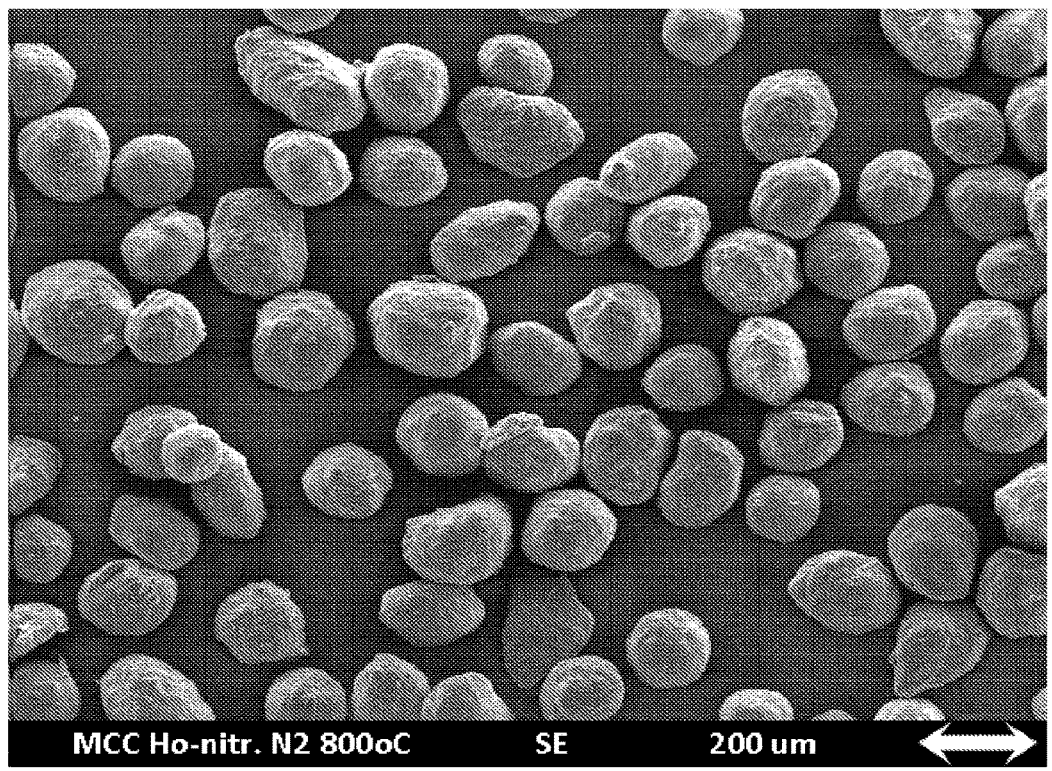
FIG. 5 shows a Scanning Electron Micrograph (SEM) picture of bodies of carbon supported holmium oxide particles of the present invention at low magnification, produced according to the following example.
Figure 6:
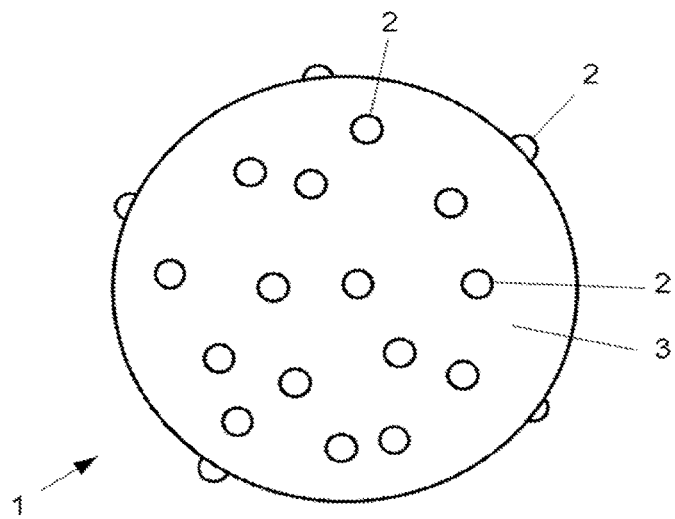
FIG. 6 shows schematically a body (1) according to the present invention comprising a porous amorphous carbon carrier particle (3) on which are present nanoparticles (2) of an oxide of lanthanide.

From the TEM-image of FIG. 1 and the HR-TEM image of FIG. 2 it is deduced that particles of a very small crystallite size (below 5 nm) are formed supported within an amorphous carbon. The STEM-image with HAADF detector (FIG. 3) shows the same. Elemental analysis (FIG. 4) shows that oxygen is abundant in the sample which suggests that holmium is present in an oxidic state. Electron diffraction (not shown) substantiates that holmium is present as $Ho_2O_3$ in a cubic crystal structure. FIG. 5 shows the bodies of the invention on a low magnification, indicating that the impregnated MCC particles have a homogeneous size distribution after pyrolysis.

The invention claimed is:

1. A process for producing bodies comprising nanoparticles of an oxide of lanthanide supported on amorphous carbon particles, which process comprises
impregnating a carbon source material by contacting it with a solution of a lanthanide salt;
drying said impregnated carbon source material; and
subjecting said dried impregnated material to pyrolysis under inert conditions.

2. The process according to claim 1, further comprising removing the amorphous carbon particles, whereby the nanoparticles are obtained in pure form.

3. The process according to claim 2, wherein the amorphous carbon particles are removed by thermal treatment in an oxygen-containing gas flow at a temperature below about 500° C.

4. The process according to claim 1, wherein the bodies have a diameter of 10-1000 micrometers.

5. The process according to claim 1, wherein the oxide of lanthanide nanoparticles have a diameter of 10 nm or less.

6. The process according to claim 1, wherein the oxide of lanthanide nanoparticles have a diameter of 5 nm or less.

7. The process according to claim 1, wherein the oxide of lanthanide is holmium oxide.

8. The process according to claim 1, wherein the oxide of lanthanide is $Ho_2O_3$.

9. The process according to claim 1, wherein the bodies are substantially spherical.

10. The process according to claim 1, wherein the bodies have a diameter of 15-500 μm.

11. The process according to claim 1, wherein the bodies have a diameter of 20-400 μm.

12. The process according to claim 1, wherein the bodies have a diameter of 25-250 μm.

13. The process according to claim 1, comprising impregnating the carbon source material by contacting it with an aqueous solution of the lanthanide salt, the solution having a lanthanide salt concentration of from 0.01 to 1.5 g/mL.

14. The process according to claim 13, wherein the concentration is from 0.1 to 1 g/mL.

15. The process according to claim 1, wherein the salt is a lanthanide nitrate.

16. The process according to claim 1, wherein the salt is holmium nitrate.

* * * * *